United States Patent [19]

Oleniacz

[11] 3,957,971

[45] May 18, 1976

[54] MOISTURIZING UNITS AND MOISTURIZING COMPOSITIONS CONTAINING THE SAME

[75] Inventor: Walter S. Oleniacz, Ringwood, N.J.

[73] Assignee: Lever Brothers Company, New York, N.Y.

[22] Filed: July 29, 1974

[21] Appl. No.: 492,369

[52] U.S. Cl. .......................... 424/70; 252/DIG. 13; 424/199; 424/204; 424/246; 424/319; 424/322; 424/343; 424/358; 424/365
[51] Int. Cl.² ...................... A61K 7/06; A61K 7/48
[58] Field of Search ....................... 424/70, 358, 365

[56] References Cited
UNITED STATES PATENTS

| | | | |
|---|---|---|---|
| 2,756,178 | 7/1956 | Verblen | 424/70 |
| 3,235,457 | 2/1966 | Laden | 424/70 X |
| 3,335,053 | 8/1967 | Weitzel | 424/365 X |
| 3,471,624 | 10/1969 | Youngblood | 424/365 X |
| 3,533,955 | 10/1970 | Pader et al. | 424/70 X |
| 3,535,427 | 10/1970 | Millar et al. | 424/365 |
| 3,590,123 | 6/1971 | Melloh et al. | 424/70 |
| 3,660,566 | 5/1972 | Vinson et al. | 424/365 |
| 3,697,644 | 10/1972 | Laiderman | 424/70 X |
| 3,835,169 | 9/1974 | Kraft et al. | 424/70 X |

*Primary Examiner*—Sam Rosen
*Assistant Examiner*—Vera C. Clarke
*Attorney, Agent, or Firm*—Kenneth F. Dusyn; James J. Farrell; Arnold Grant

[57] ABSTRACT

Moisturizing units capable of moisturizing and improving flexibility, plasticity, and softness of keratinous matter, particularly mammalian skin, comprise liposomes, each having a matrix of a ternary lipid mixture of lecithin, dicetyl phosphate, and a sterol, and having cavities disposed within the liposome, the cavities containing a humectant such as sodium pyroglutamate, in an aqueous medium. The moisturizing liposomes function osmotically, serving as traps for water, which may be shared with the keratin constituents as required.

17 Claims, No Drawings

MOISTURIZING UNITS AND MOISTURIZING COMPOSITIONS CONTAINING THE SAME

BACKGROUND OF THE INVENTION

1. Field of the Invention

A soft and supple skin has a marked cosmetic appeal and is an attribute of normal-functioning epidermis. The outer layer of the epidermis, or stratum corneum, can become brittle, dry, and flaky, due to loss of water. Emollients, such as fats, phospholipids, sterols, and the like were at one time thought to be substances essential to the maintenance or restoration of softness and flexibility of the skin. More recently however, investigators have become aware that dry-appearing and flaky skin is the result of loss of water-soluble natural substances, mostly humectants, from the skin. Loss of water-soluble substances from the skin can occur when the skin is exposed to adverse conditions. When this happens the stratum corneum, although it is somewhat hygroscopic and absorbs water vapor, cannot retain moisture, and soon loses it if the atmosphere becomes drier. In any event, the stratum corneum which has lost humectants does not ordinarily absorb and retain sufficient moisture for restoration to a normal condition, and the need is evident for an artificial moisturizing system for persons who suffer from dry, chapped and flaky skin, or from dry and brittle hair and nails.

2. Discussion of the Prior Art

I. H. Blank, in J. Invest. Dermatol., vol. 18, 433 (1952), presented evidence that water is the only plasticizer of skin, and that a diminished water content results in a cornified epithelium having the undesirable properties of dryness, hardness, and brittleness.

Largely as a result of the work of Blank, mentioned above, there has been investigated many factors relating to the relationship of the water content of the stratum corneum to skin flexibility and plasticity. Information obtained during the two decades following Blank's work has been summarized by B. Idson, in Drug, Cosm. Ind. vol. 104(6), page 44, vol. 105(1) page 48, and vol. 105(2), page 48, all published in 1969.

The ability of normal healthy stratum corneum to retain water has been ascribed to the presence therein of water-soluble substances having strong hygroscopic properties. Many such substances occur together in the stratum corneum and collectively have been termed the "natural moisturizing factor" by O. K. Jacobi, in Proc. Sci. Sect. T.G.A. vol. 31, 22(1959) and in J. Soc. Cosm. Chem. vol. 18, 149 (1967).

Most of the water-soluble substances comprising the natural moisturizing factor have been identified by H. W. Spier and G. Pascher in the text "Aktuelle Probleme der Dermatologie", vol. I, pp. 1–46, published by S. Karger AG, Basel/New York, 1959.

More recently, G. Smeenk and A. M. Rijnbeek in Acta derm-venereol., vol. 49, 476 (1969) have published information indicating that the hygroscopic properties of the water-soluble corneum fraction are due to the simultaneous presence, in physiological proportions, of the components reported by Spier and Pascher, mentioned above.

It is known that a lipid membrane or covering in the stratum corneum hinders the extraction of the water-soluble substances therefrom by water, as reported by E. J. Singer and L. J. Vinson in Proc. Sci. Sect. T.G.A. vol. 46, 29 (1966), and by I. H. Blank, J. Invest. Dermatol., vol. 21, 259 (1953).

G. Sessa and H. Weissmann, in J. Lipid Res., vol. 9, 310 (1968), describe liposomes and discuss the rate of diffusion of ions across the lipid layers thereof.

U.S. Pat. No. 3,231,472 discloses the use of a synthetic skin moisturizer prepared by condensing an amino acid with a reducing sugar to provide an N-glycoside and thereafter contacting the N-glycoside with a proton donor.

SUMMARY OF THE INVENTION

The common dry skin condition is attributable to various factors including (a) the external atmospheric relative humidity, (b) disorganization of lipid membranes, and (c) disruption of lipid membranes plus loss of water-soluble hygroscopic substances. When the external relative humidity is low, there is rapid water loss from the skin to external environment although the moisturizing system of the skin exists in its normal physical state. Water is lost from the skin at a faster rate than it can be replaced by migration from the underlying dermal tissues. More commonly, dry skin is a consequence of exposure to environmental agents capable of disrupting the physical state of the moisturizing system. For example, non-aqueous solvents and aqueous solutions of strong washing products contribute to a dry skin condition by damaging the lipid membranes, allowing the leaching out of water-soluble substances when the skin is immersed in water.

For alleviation of the dry skin condition, it is necessary to restore water to the skin. If the physical state of the skin's moisturizing system is normal, or only the lipid membranes damaged, then water retention can be increased by applying an occlusive film to the skin surface. The occlusive film retards the rate of water vapor diffusion from the skin to the outside environment. The use of water-soluble hygroscopic compounds, per se, for moisturizing skin is not of practical value since such agents lack the property of skin substantivity by virtue of their high degree of water solubility.

Dry, rough, chapped and scaly skin areas are substantially devoid of natural humectants, and although water vapor can migrate to these areas from the underlying skin it is not retained, but is lost to the atmosphere. If a lipid layer is superimposed over these areas, water may still escape, since it is practically impossible to maintain an unbroken film of lipid.

The application to the skin of humectants alone is unsatisfactory since these are not skin-substantive, and are readily rinsed off.

The problems of non-substantivity and loss of water migrating from the underlying skin are solved by the use of the liposomes described herein. The liposomes are substantive to keratinous matter and moreover do not depend upon absorption of water from the skin alone but function to absorb water from the atmosphere in addition to providing their own water content, and share the water with the keratinous matter to which they are applied.

When applied to keratinous matter, moisturization, softness and flexibility are imparted or maintained by the liposomes, which comprise a matrix of a lipid mixture, having a plurality of cavities therein containing a humectant in aqueous solution.

It is therefore an object of the invention to provide compositions capable of moisturizing keratinous matter.

It is another object of the invention to provide compositions capable of improving the softness, plasticity, and flexibility of water-deficient stratum corneum.

It is still another object of the invention to provide a process for moisturizing and improving or maintaining the flexibility of living keratinous matter by applying to the keratinous matter a multiplicity of the liposomes described hereinbelow.

It is a further object of the invention to provide a composition containing a moisturizing humectant for keratinous matter and an occlusive substance to retard the rate of water evaporation.

Accordingly the invention provides a composition having a moisturizing humectant to supply water to, or replace water lost by keratinous matter, and an occlusive substance to retard the rate of water loss. The composition is a liposome comprising a matrix of a ternary lipid mixture of lecithin, dicetyl phosphate, and a sterol, and having cavities disposed internally of said liposome, said cavities containing a humectant dissolved in an aqueous medium. The surface of the liposome is substantially continuous.

DETAILED DESCRIPTION OF THE INVENTION

The sizes of the liposomes with which the present invention is concerned vary somewhat, depending upon the species of lipid, species of humectant, and type and intensity of the mechanical agitation used to form the liposomes.

Liposomes may be prepared by the following procedure.

A desired weight of a mixture of soybean lecithin, dicetyl phosphate, and a sterol, as described hereinafter, in predetermined molar ratios is dissolved in chloroform in a round bottom flask of suitable size. The chloroform is removed by evaporation, and there are added for each mole of residue, about 60–80 moles of a humectant in the form of a 0.145 molar aqueous solution at pH 5.3. The flask is shaken for 6 hours at 40 strokes per minute on a shaker bath at a temperature of 25°C whereupon the lipids swell in the aqueous solution to form liposomes having structures described hereinbelow. To induce additional swelling of the liposomes the suspension is held at 5°C for 18 hours without shaking. The suspension is then dialyzed for 5 hours against four 800-ml changes of 0.145M NaCl to remove any excess humectant not incorporated into the liposomes.

Suitable humectants for use in the present invention are for example glycerol, urea, sodium pyroglutamate (2-pyrrolidone-5-carboxylic acid, sodium salt), ornithine [$H_2N(CH_2)_3CH(NH_2)COOH$, m.w. 132.16], and the Spier-Pascher water solubles consisting of a mixture of the following substances in the indicated proportions.

| | mM/100g corneum |
|---|---|
| alanine | 8.4 |
| arginine·HCl | 1.7 |
| aspartic acid | 4.8 |
| citrulline | 7.3 |
| glutamic acid | 1.9 |
| glyocoll | 11.5 |
| histidine·HCl | 4.4 |
| leucine | 3.1 |
| lysine·HCl | 1.2 |
| ornithine·HCl | 1.5 |
| phenylalanine | 1.1 |
| proline | 1.7 |
| serine | 23.9 |

-continued

| | mM/100g corneum |
|---|---|
| threonine | 4.3 |
| tryptophan | 0.5 |
| tyrosine | 1.7 |
| valine | 2.3 |
| calcium chloride | 10.1 |
| citric acid | 0.095 |
| creatinine | 0.1 |
| glucosamine | 0.1 |
| glucose | 1.1 |
| lactic acid | 17.8 |
| magnesium chloride | 1.9 |

| | mM/100g corneum |
|---|---|
| magnesium chloride | 1.9 |
| sodium phosphate (dibasic) | 0.3 |
| ammonium chloride | 1.1 |
| 2-pyrrolidone-5-carboxylic acid | 14.2 |
| ribose | 0.3 |
| urea | 9.0 |
| uric acid | 0.1 |
| urocanic acid | 4.8 |

The lecithin used in the examples described herein is commercial lecithin derived from soybean oil and contains cephalin, choline lecithin, and inositol phosphatides. The use of lecithin in cosmetics is discussed by G. T. Walker in American Perfumer and Cosmetics, vol. 82, pages 73–76, October, 1967.

Suitable sterols for use in the lipid mixture are cholesterol, phytosterol, sitosterol, sitosterol pyroglutamate, 7-dehydrocholesterol, and lanosterol. It is also possible to use caprolactum.

The lipid membranes preferably are ternary mixtures of lecithin, dicetyl phosphate, and a sterol selected from the group listed hereinabove, in the preferred molar ratios of 70:20:10, respectively. The molar percentage of lecithin may range from about 50% to about 80%, the dicetyl phosphate from about 10% to about 30%, and the sterol from about 10% to about 30%, basis for ternary lipid mixture. Lecithin is employed to take advantage of its property of swelling in salt solutions. Dicetyl phosphate has the property of imparting a negative charge to the lipid membranes so that the mutual repulsive action of opposing channel surfaces widens the channels. The sterol functions as an occlusive film when the liposomes are applied to skin or hair.

The gross appearance of the liposomes useful in the practice of the present invention is that of an opalescent suspension having a milky while color.

The components which constitute the lipid matrix, or membrane, and the aqueous humectant phase are commercially available or may readily be prepared. L-pyroglutamic acid may be purchased from Nutritional Biochemicals Corporation, Cleveland, Ohio; dicetyl phosphate and commercial grade soybean L-alpha-lecithin may be obtained from Sigma Chemical Company, St. Louis, Mo.; beta-sitosterols are supplied by Upjohn Co., Kalamazoo, Mich.; cholesterol is purchased from Mann Research Laboratories, Inc., New York, N.Y.; caprolactam is supplied by Pfaltz-Bauer, Inc., Flushing, N.Y.; lanosterol, 7-dehydrocholesterol, and ornithine are obtained from Calbiochem, Los Angeles, Calif.

Sitosterol pyroglutamate may be made by the following procedure. One hundred grams, about 0.25 mole, of sitosterol are dissolved in 500 ml of benzene together with 5 grams of paratoluenesulfonic acid as catalyst, and 65 grams, 0.5 mole, of pyroglutamic acid. The mixture is refluxed for 10 hours, and under azeotropic conditions 5 ml of water are collected. The reaction mixture is filtered to remove unreacted pyroglutamic acid, which is then washed with hot benzene and the washings are added to the main filtrate. The benzene is evaporated to dryness on a steam bath. The residue is crystallized from 1500 ml of acetone, producing a tan-colored powder. A volume of 1500 ml methanol is added to the powder and heated to boiling. The powder is allowed to settle and the methanol decanted. The powder is treated with four additional portions of methanol, 400 ml each, decanting each time, and filtering after the last treatment, yielding 27.7 grams of tan-colored powder. Analysis for nitrogen shows 2.49% N (theoretical 2.67%). Some impurities are indicated by NMR analysis.

As demonstrated in Example 13 below, the amphoteric and anionic detergents are suitable for use in the shampoos useful as a cosmetically acceptable vehicle for applying the liposomes to the hair. Suitable amphoteric detergents include N-lauryl-N'-carboxymethyl-N'-(2-hydroxyethyl)ethylenediamine, coco-beta-alanine, the alkali-metal salts of protein-coconut fatty acid condensates, aminopropionates such as alkyl beta-iminodipropionates represented by $RN(CH_2CH_2COOM)_2$ and alkyl beta-iminopropionates represented by the formula $RNHCH_2CH_2COOM$, wherein R is an aliphatic hydrocarbon radical having about 8 to about 18 carbon atoms and M is a cation to neutralize the charge on the anion and to render the detergent compound water soluble. Suitable anionic detergents are the water-soluble anionic sulfate, sulfonate and carboxylate foaming detergents mentioned in the literature, such as the texts "Surface Active Agents" by Schwartz and Perry, and "Surface Active Agents and Detergents" by Swartz, Perry and Berch, both Interscience Publishers, New York, the disclosures of which are incorporated herein by reference.

The liposomes may be applied in the form of an aqueous suspension as prepared, or may be applied in a composition comprising a physiologically acceptable vehicle into which the liposomes have been incorporated. The physiologically acceptable vehicle may be a skin lotion or cream, such as a cold cream, vanishing cream, cleansing cream, etc., for application to the skin. The vehicle may be a shampoo or brilliantine for application to the hair.

The above-mentioned compositions may be prepared by the usual procedures known to those skilled in the art, using however the precaution to maintain the temperature of the mixture below the melting point of the liposomes from the time the liposomes are incorporated.

The term "moisturize" or derivatives thereof, relates to the conservation or enhancement of the water content of the keratinous matter of living mammals, with particular reference to the stratum corneum, hair, and nails of human beings.

The term "humectant" is used herein in its usual sense, and particularly refers to water-soluble, physiologically acceptable, substances which are hygroscopic and capable of spontaneously absorbing water vapor.

"Occlusion" is a term used herein to indicate the trapping of water in the keratinous matter by a layer of a water-impervious fatty substance.

By "skin cream" is meant a spreadable composition in either paste or liquid form, adaptable to be spread over the skin with the object of imparting or maintaining a desirable characteristic.

The invention may be more fully understood by reference to the following Examples.

EXAMPLE 1

A weight of 0.0602 gram of a ternary mixture of 70 molar proportions (0.0455 gram) of soybean lecithin, 20 molar proportions (0.0109 gram) of dicetyl phosphate, and 10 molar proportions (0.0038 gram) of cholesterol is placed in a one-liter round bottom flask and dissolved in 10 ml of chloroform. The chloroform is evaporated and 50 ml of a 0.145 molar aqueous sodium pyroglutamate solution having a pH of 5.3 are added to film of lipid residue remaining after evaporation of the chloroform. The flask is shaken until the lipids swell in the aqueous medium and the film is removed from the walls of the flask, whereby liposomes are formed. The flask and contents are then held for 18 hours at a temperature of 5°C without shaking to permit additional swelling of the liposomes. The liposome suspension is then dialyzed for five hours against four 800-ml changes of 0.145M NaCl to remove any sodium pyroglutamate not bound in the liposomes.

Light microscopy of stained wet mounts of liposomes prepared as above shows that the liposomes are in the smectic mesophase or wet liquid crystal state. Structurally the liposomes are observed to be microscopic spherules bound by a phospholipid-cholesterol membrane.

The water-binding characteristics of the above-described liposomes are the same as those of the humectant employed, i.e., sodium pyroglutamate.

The above-described liposomes restore the in vitro water-binding capacity of damaged corneum membranes as shown by the following test.

Ten neonate rat corneum membranes having dry weights from 8.2 to 18.8 milligrams are damaged by exposure to an aqueous 40% by volume solution of tetrahydrofuran. This treatment removes 1.7 to 4.9 milligrams of the corneum membranes, dry basis, and greatly reduces the water-binding capacities of the membranes, as shown in Table I, below. The above-described liposomes are applied uniformly over the membranes in amounts equal to the weight of membrane removed by the tetrahydrofuran treatment, dried over phosphorus pentoxide at 25°C, and allowed to remain 24 hours in a closed vessel at 81% relative humidity at 25°C. The membranes are then weighed, and the amount of imbibed water calculated.

Table I, below, shows the extent to which the water-binding capacity of the animal membranes is reduced when the membrane is damaged by tetrahydrofuran (column 3) and the extent to which the water-binding capacity is restored by the liposome treatment described above (column 4).

TABLE I

MILLIGRAMS WATER BOUND PER 100 MILLIGRAMS OF DRY MEMBRANE

| Column 1 Membrane No. | Column 2 Before Damage | Column 3 Damaged | Column 4 Damaged Followed by Liposome Treatment |
| --- | --- | --- | --- |
| 1 | 33.9 | 0.9 | 54.8 |
| 2 | 33.3 | 6.1 | 54.1 |
| 3 | 30.5 | 5.1 | 22.8 |
| 4 | 27.8 | 3.9 | 68.3 |
| 5 | 22.6 | 6.3 | 56.2 |
| 6 | 29.4 | 4.2 | 44.3 |
| 7 | 30.4 | 3.0 | 34.2 |

TABLE I-continued

MILLIGRAMS WATER BOUND PER 100 MILLIGRAMS OF DRY MEMBRANE

| Column 1 Membrane No. | Column 2 Before Damage | Column 3 Damaged | Column 4 Damaged Followed by Liposome Treatment |
|---|---|---|---|
| 8 | 29.0 | 8.2 | 56.2 |
| 9 | 29.5 | 5.3 | 47.4 |
| 10 | 29.2 | 4.2 | 32.0 |

The foregoing data show that the water-binding capacity of normal corneum membranes is substantially constant among the 10 specimens tested (column 2). Damaging the membranes by treatment with tetrahydrofuran sharply reduces the water-binding capacity, as seen in column 3. The figures in column 4 show the water-binding capacities of the membranes after treating the damaged membranes with liposomes prepared as described above. For 9 out of the 10 specimens, the water-binding capacities are improved to levels above the initial capacities, i.e., from about 110% to about 240% of the initial values.

EXAMPLES 2-10

Liposomes having the lipid and aqueous components shown below are prepared by the procedure described in Example 1. The lipid components in each instance are a ternary mixture of lecithin, dicetyl phosphate, and sterol in the molar ratios of 70:20:10, respectively. In Example 8, the sterol component is a mixture.

| Example No. | Sterol | Humectant |
|---|---|---|
| 2 | cholesterol | ornithine |
| 3 | cholesterol | 1:1 weight ratio of sodium pyroglutamate and ornithine |
| 4 | cholesterol | Spier-Pascher water-solubles |
| 5 | sitosterol pyroglutamate | sodium pyroglutamate |
| 6 | sitosterol | sodium pyroglutamate |
| 7 | caprolactam | sodium pyroglutamate |
| 8 | 1:1 weight ratio of caprolactam and cholesterol | sodium pyroglutamate |
| 9 | 7-dehydrocholesterol | sodium pyroglutamate |
| 10 | lanosterol | sodium pyroglutamate |

All of the liposomes prepared as in Examples 1-10 above are spherules variously ranging in size from about 0.5 to about 12 microns in diameter. The liposomes of Example 4, containing Spier-Pascher water-solubles, tend to be the smallest spherules in this range, the liposomes of Example 1 are in general intermediate in size, while the remaining are in the upper region of the aforesaid range.

All of the aforementioned liposomes are characterized by their ability to absorb water, a property determined by the following test procedure.

One ml of the prepared liposome suspensions is placed in each of several aluminum weighing pans and dried to constant weight over phosphorus pentoxide at 25°C. Three pans from each of Examples 1-10 are placed in closed containers having the relative humidities at 25°C therein regulated at 52% by a saturated aqueous sodium dichromate solution, 81% by a saturated aqueous ammonium sulfate solution, and 98% by a saturated aqueous lead nitrate solution. After exposure for 24 hours, the pans are again weighed and the amount of water imbibed calculated. The results are presented in Table II below.

TABLE II

WATER-BINDING CAPACITY OF LIPOSOMES
Weight Increase in Percent of Initial Liposome Weight (Approximate)

| Example No. | 52%RH | 81%RH | 98%RH |
|---|---|---|---|
| 1 | 100 | 253 | 350 |
| 2 | 100 | 231 | 352 |
| 3 | 100 | 268 | 472 |
| 4 | 100 | 280 | 536 |
| 5 | 100 | 246 | 379 |
| 6 | 100 | 318 | 435 |
| 7 | 100 | 239 | 398 |
| 8 | 100 | 244 | 418 |
| 9 | 100 | 241 | 413 |
| 10 | 100 | 261 | 427 |

A comparison of the water-binding capacities at 98% relative humidity shows that the liposomes having the mixture of Spier-Pascher water-solubles are the most effective humectants of the group tested, holding 5.5 times their weight of water, as compared with the remaining nine liposome compositions which held about 4 times their weight of water.

The function of the sterol component has been explained hereinabove as being that of an occlusive film which forms when the liposomes are applied to the skin or hair. Inspection of the data at 98% relative humidity shows that, among the liposomes having in common sodium pyroglutamate as the humectant, namely those of Examples 1 and 5 through 10, the most effective occlusive agents are sitosterol, 7-dehydrocholesterol, and lanosterol.

EXAMPLES 11-14

Examples 11 through 14 further illustrate the efficacy of liposomes of the present invention as moisturizing agents. Example 11 shows that the liposomes are effective moisturizers when deposited in in vitro tests on animal stratum corneum from an aqueous medium at a temperature of 40°C, this being the temperature approximating the 105°F reported by Suskind and Whitehouse, (Arch. Dermat. Vol. 88, 66 (1963)) as being the temperature commonly used in the bath and ordinary household chores.

Example 12 shows that the liposomes can be deposited on animal stratum corneum membranes that have been damaged by treatment with tetrahydrofuran, and that the deposited liposomes enhance the water-binding capacity of the damaged corneum.

EXAMPLE 11

Fifteen membranes of rat stratum corneum are immersed in a 1% suspension of liposomes, prepared as described in Example 1, at a temperature of 40°C for a time of 30 minutes with agitation. The membranes are then rinsed in distilled water at room temperature for 10 minutes. Each individual membrane is pretreated in the foregoing manner, but without liposome deposition, to serve as a control for determining the extent of liposome deposition and the increase in water-binding capacity.

Table III, below, shows the increase in dry weight of the corneum membranes, indicating deposition of the liposome spherules on the membrane. The water-bind-

TABLE IV

| | UNDAMAGED | | WATER DIFFUSION RATES[a] DAMAGED (a) 2-hour tetrahydrofuran treatment | | DAMAGED (b) 30-minute tetrahydrofuran treatment | | DAMAGED (c) Soap treatment | |
|---|---|---|---|---|---|---|---|---|
| | without liposomes | with liposomes | without liposomes | with liposomes | without liposomes | with liposomes | without liposomes | with liposomes |
| A | 0.20 | 0.20 | 12.5 | 9.36 | 8.74 | 3.47 | 2.00 | 0.86 |
| B | 0.23 | 0.29 | 12.8 | — | 9.30 | 3.56 | 2.26 | 1.47 |
| C | 0.33 | 0.29 | 11.4 | 9.47 | 8.34 | 3.30 | 2.67 | 1.06 |
| D | 0.26 | 0.31 | 11.8 | — | 8.90 | 3.60 | 3.18 | 1.16 |
| E | 0.19 | — | 12.5 | 9.11 | — | — | — | 1.26 |
| Mean | 0.20 | 0.24 | 12.2 | 9.31 | 8.82 | 3.48 | 2.52 | 1.16 |

[a] Figures are milligrams of water diffused through one square centimeter of corneum per hour.

ing data indicate that the liposome deposition increases the water-binding capacity of the corneum membranes.

The procedure for determining the moisturizing effect is described in Example 1.

TABLE III

IN VITRO ENHANCEMENT OF THE WATER-BINDING CAPACITY OF STRATUM CORNEUM MEMBRANES

| Untreated | Liposome Treated | | |
|---|---|---|---|
| mg. water bound per membrane | mg. material deposited | mg. water bound per membrane | water bound in percent of control |
| 2.65 | 0.65 | 3.65 | 137.7 |
| 3.25 | 0.85 | 4.40 | 135.3 |
| 2.30 | 1.35 | 2.60 | 113.0 |
| 2.10 | 1.45 | 2.50 | 119.0 |
| 2.60 | 1.75 | 2.40 | 109.0 |
| 1.90 | 1.10 | 1.60 | 110.0 |
| 2.60 | 0.75 | 2.35 | 109.3 |
| 1.75 | 1.65 | 2.10 | 120.0 |
| 2.90 | 2.70 | 3.40 | 117.2 |
| 2.45 | 1.25 | 2.95 | 120.4 |
| 2.80 | 0.80 | 3.35 | 119.6 |
| 2.15 | 0.95 | 2.35 | 109.3 |
| 2.60 | 1.25 | 3.50 | 134.6 |
| 2.90 | 0.80 | 3.15 | 108.6 |
| 2.35 | 0.95 | 2.70 | 114.8 |

The foregoing figures represent the percentage of water bound in each membrane relative to its own control.

EXAMPLE 12

This example shows the beneficial action of liposomes on damaged stratum corneum.

Rat stratum corneum membranes having known water-binding capacities are damaged to varying degrees by (a) immersion in 37% aqueous tetrahydrofuran for 2 hours, producing virtual barrier destruction, (b) immersion in the same medium for 30 minutes, resulting in an intermediate grade of barrier destruction, and (c) immersion in an 8% solution of a commercial bar soap for 30 minutes at 40°C, causing a relatively mild degree of barrier damage. Following these treatments, the membranes are rinsed in distilled water for 10 minutes, dried, and the extent of reduction in water-binding capacity at 81% relative humidity and 25°C ascertained.

The membranes treated as above are again dried, and then immersed in a 1% suspension of liposomes prepared as in Example 1 for 30 minutes at 25°C with agitation and rinsed for 10 minutes. The treated membranes are dried, weighed, and subjected for 24 hours to an atmosphere having a temperature of 25°C and 81% relative humidity, then reweighed, as described in Example 1.

The results are recorded in Table IV. The liposomes effect partial barrier restoration on the damaged membranes as shown by the decreased rate of water diffusion through the liposome-treated damaged membranes as compared with diffusion through the damaged membrane before the liposome treatment. The figures in the first two columns of Table IV show that the liposomes have no effect on the barrier properties of undamaged stratum corneum.

The rate of water diffusion is determined by the following procedure, using the Sage Moisture Meter, described by Baker and Kligman in Arch. Derm., Vol. 96, page 441 (1967). The membrane (skin) is stretched tightly in sealed position over the chamber, which contains water. A current of dry air flowing at the rate of 0.025 liter per minute is swept over the membrane and is directed through a series of hygrometers which measure the relative humidity of the air that has passed over the membrane. Using the relative humidity data, the amount of water vapor that has diffused through the membrane in a selected time interval is calculated.

EXAMPLE 13

This example shows the effect of a representative amphoteric, anionic, nonionic, and quaternary ammonium surfactant on the barrier properties of the lipid matrix of the liposomes within the invention.

The data below are obtained by a modification of the procedure described by Weissmann et al in Nature, Vol. 208, 649 (1965). In the present study, the release of radioactive glutamic acid from the liposomes on exposure to solutions of the surfactants is measured to determine the extent of membrane damage. One-ml portions of dialyzed liposomes containing as the aqueous component a solution of $^{14}$C-glutamic acid, and otherwise prepared as described in Example 1, are placed in several small dialysis sacs. A solution of 0.6 gm. of each test surfactant in 100 ml of distilled water is prepared and 0.2 ml of each solution is dispensed into separate sacs. The final surfactant concentration is 0.1% (weight volume). Following the addition of the surfactant, the contents of the sacs are tied, placed in small narrow bore test tubes containing 5.0 ml of a 0.145 molar solution of equimolar NaCl and KCl, and held at 37°C. At 15-minute intervals, the sacs are transferred to tubes containing fresh NaCl/KCl solutions of the above strength. The $^{14}$C-glutamic acid which diffuses into the salt solution in each period is determined by liquid scintillation counting.

The results are presented in Table V below. It will be noted that the amphoteric and anionic surfactants do not disrupt the liposomal membrane since the leakage rate of the $^{14}$C-glutamic acid is comparable to that of the control tested without a surfactant. The nonionic causes slight membrane damage, and the quaternary produces marked damage.

The amphoteric detergent tested is Miranol C-2M, a trademark of the Miranol Chemical Company, Inc., Irvington, N.J. The compound is described as lauroyl-cycloimidinium-1-ethoxyethionic acid -2-ethionic acid, disodium salt, by the manufacturer, and is a compound described in U.S. Pat. No. 2,773,068.

The anionic detergent is secondary alkylbenzene sulfonate wherein the benzene ring is randomly positioned, except terminally, along a linear alkyl chain of about 13 carbon atoms.

The nonionic is Pluronic L-64, a trademark of the

TABLE V

THE EFFECTS OF SURFACTANTS ON THE STABILITY OF LIPOSOMAL MEMBRANES AT 37°C[a]

| Time(min) | Control[b] | Miranol C-2M[c] Amphoteric | LAS Anionic | Pluronic L-64 Nonionic | Arquad 2C-75 Quaternary |
|---|---|---|---|---|---|
| 15 | 432 | 460 | 382 | 572 | 1899 |
| 30 | 826 | 803 | 718 | 1122 | 3551 |
| 45 | 1109 | 1065 | 1077 | 1492 | 4750 |
| 60 | 1351 | 1323 | 1319 | 1802 | 5747 |
| 75 | 1552 | 1564 | 1522 | 2123 | 6622 |
| 90 | 1739 | 1748 | 1711 | 2371 | 7305 |
| 105 | 1912 | 1902 | 1872 | 2569 | 7875 |
| 120 | 2048 | 2030 | 2013 | 2743 | 8358 |

[a]Surfactant damage to the liposomal membranes was determined by monitoring the release of $^{14}C$-glutamic acid over the time intervals indicated.
[b]Controls consisted of liposomes suspended in 0.145M NaCl/KCl solution.
[c]Liposome suspensions (0.145M NaCl/KCl) contained test surfactants at a final concentration of 0.1%.

Wyandotte Chemical Company. Pluronic L-64 is a compound having the empirical formula $HO(C_2H_4O)_a(C_3H_8O)_b(C_2H_4O)_cH$ prepared by condensing ethylene oxide with a hydrophobic base formed by the condensation of propylene oxide with propylene glycol where $b$ is 26–30. The molecular weight of the base unit $(C_3H_8O)_b$ is about 1501 to about 1800, and $a$ plus $c$ is an integer such that the molecule contains 40% to 50% ethylene oxide.

The quaternary is Arquad 2C-75, a trademark of Armour and Company. The compound is dicocodimethyl ammonium chloride, the term "dicoco" indicating two long-chain alkyl groups having the carbon chain distribution of coconut oil.

EXAMPLE 14

This example shows the beneficial action of the liposomes of the present invention on the skin of human subjects.

Liposomes prepared as in Example 1 are applied to the rough, red, dry, cracked skin of one hand of each of two human subjects. A cooling sensation is noted upon the application of the liposomes. The treated hands are rinsed, blotted dry, and the condition of the skin observed about 18 hours following treatment. In both instances, the skin of the treated hand feels softer and visually appears less cracked and scaly than the skin of the untreated hand of the same person.

EXAMPLE 15

Following is an example of a shampoo within the invention.

| | Percent by Weight |
|---|---|
| Triethanolammonium lauryl sulfate | 20 |
| Ethanol | 20 |
| Bis(2-hydroxyethyl)alkylamine oxide wherein the alkyl group is a mixture of predominantly $C_{12}$ and $C_{14}$ chain lengths | 5 |
| Liposomes in aqueous medium[a] | 55 |
| | 100 |

[a]prepared as in Example 1, but omitting the dialysis against NaCl. The liposomes thus prepared are at a 0.12% weight/volume concentration in 0.145 molar sodium pyroglutamate solution.

The shampoo is prepared by merely mixing the four components together at room temperature, maintaining the pH between 5 and 6, until the solid components have dissolved.

EXAMPLE 16

Following is an example of a hand lotion composition within the invention.

| | Percent by Weight |
|---|---|
| Oil Phase | |
| Amerlate P[a] | 0.5 |
| Glyceryl monostearate, neutral | 2.0 |
| Stearic acid, triple pressed | |
| Water Phase | |
| Triethanolamine | 1.0 |
| Propylene Glycol | 5.0 |
| Liposomes in aqueous medium[b] | 88.5 |
| | 100.0 |

[a]Trademark of American Cholesterol Products, Inc. Isopropyl ester of a mixture of normal, branched chain and hydroxy acids of lanolin.
[b]as in Example 15.

The liposome suspension is warmed to about 45°C, the triethanolamine and the propylene glycol are added, followed immediately by the stearic acid, glyceryl monostearate, and Amerlate, in that order, while mixing. Mixing is continued until a smooth cream is obtained.

EXAMPLE 17

Following is an example of a hand cream within the invention.

| | Percent by Weight |
|---|---|
| Oil Phase | |
| Amerchol L-101[a] | 6.0 |
| Modulan[b] | 2.0 |
| Glyceryl monostearate, neutral | 12.0 |
| Petrolatum, USP White | 4.0 |
| Mineral oil, visc. 70 cps | 5.0 |
| Stearic acid, triple pressed | 5.0 |
| Water Phase | |
| Glycerine | 5.0 |
| Sodium lauryl sulfate | 0.5 |

-continued

| | Percent by Weight |
|---|---|
| Liposomes in aqueous medium[c] | 60.5 |
| | 100.0 |

[a]Trademark of American Cholesterol Products, Inc. Mixture of lanolin sterols and complex higher alcohols.
[b]Trademark of American Cholesterol Products, Inc. Acetylated USP lanolin (U.S. Patent No. 2,725,334).
[c]as in Example 14.

The components of the water phase are mixed together and warmed to 85°C. The components of the oil phase are melted together and poured into the water phase with mixing. Mixing is continued until a smooth cream is obtained.

EXAMPLE 18

Following is a brilliantine composition containing liposomes within the invention.

| | Percent by Weight |
|---|---|
| Glycerine | 35 |
| Alcohol | 30 |
| Liposomes in aqueous medium[a] | 34 |
| Perfume | 1 |
| | 100 |

[a]Prepared as in Example 7, as a 0.12% weight/volume concentration.

The composition is prepared by merely mixing the components.

EXAMPLE 19

The composition of a vanishing cream containing liposomes of the present invention is as follows.

| | Percent by Weight |
|---|---|
| Stearic acid | 20 |
| Potassium stearate | 5 |
| Glycerine | 15 |
| Liposomes in aqueous medium[a] | 60 |
| | 100 |

[a]Prepared as in Example 4, as a 0.12% weight/volume concentration.

The glycerine and the liposomes are mixed together and warmed to 45°C. The potassium stearate is then added followed by the molten stearic acid, with mixing. Mixing is continued until a smooth paste is obtained.

EXAMPLE 20

The composition of a cleansing cream containing liposomes of the present invention is as follows.

| | Percent by Weight |
|---|---|
| Mineral oil | 47 |
| Beeswax | 10 |
| Stearic acid | 2 |
| Borax | 1 |
| Liposomes in aqueous medium[a] | 40 |
| | 100 |

[a]Prepared as in Example 10 as a 0.12% weight/volume concentration.

The borax is dissolved in the liposome suspension and the melted stearic acid added with stirring. The beeswax is added to the mineral oil and heated to complete liquefication. This mixture is then added to the aqueous portion with stirring. Stirring is continued until a smooth cream is obtained.

Having described the invention, those skilled in the art will know modifications within the spirit thereof, and the invention is to be limited only within the scope of the appended claims.

What is claimed is:

1. A liposome comprising
   i. a matrix of a ternary lipid mixture comprising about 50 to about 80 molar proportions of lecithin; about 10 to about 30 molar proportions of dicetyl phosphate; and about 10 to about 30 molar proportions of a sterol or caprolactum, said sterol being selected from the group consisting of cholesterol, phytosterol, sitosterol, sitosterol pyroglutamate, 7-dehydrocholesterol, lanosterol and mixtures thereof; and
   ii. an aqueous solution of a humectant disposed interiorly of said liposome, said humectant being selected from the group consisting of glycerol, urea, sodium pyroglutamate, ornithine, and the Spier-Pascher water solubles;
   said liposome having a substantially continuous outer surface.

2. A method for moisturizing keratinous matter of a living mammal comprising applying to said keratinous matter an effective amount of the liposome claimed in claim 1.

3. The liposome in accordance with claim 1 wherein said sterol is cholesterol.

4. The liposome in accordance with claim 1 wherein said sterol is phytosterol.

5. The liposome in accordance with claim 1 wherein said sterol is sitosterol.

6. The liposome in accordance with claim 1 wherein said sterol is sitosterol pyroglutamate.

7. The liposome in accordance with claim 1 wherein said sterol is 7-dehydrocholesterol.

8. The liposome in accordance with claim 1 wherein said sterol is lanosterol.

9. The liposome in accordance with claim 1 wherein said humectant is glycerol.

10. The liposome in accordance with claim 1 wherein said humectant is urea.

11. The liposome in accordance with claim 1 wherein said humectant is sodium pyroglutamate.

12. The liposome in accordance with claim 1 wherein said humectant is ornithine.

13. The liposome in accordance with claim 1 wherein said humectant is the Spier-Pascher water-solubles.

14. A composition capable of moisturizing keratinous matter of a living mammal, comprising an effective amount of the liposome described in claim 1 in a physiologically acceptable vehicle.

15. The composition in accordance with claim 14 wherein said vehicle is a skin cream.

16. The composition in accordance with claim 14 wherein said vehicle is a shampoo.

17. The composition in accordance with claim 14 wherein said vehicle is a brilliantine.

* * * * *